US010968184B2

(12) United States Patent
Guillemont et al.

(10) Patent No.: US 10,968,184 B2
(45) Date of Patent: Apr. 6, 2021

(54) PYRIMIDINE PRODRUGS FOR THE TREATMENT OF VIRAL INFECTIONS AND FURTHER DISEASES

(71) Applicant: Janssen Sciences Ireland Unlimited Company, County Cork (IE)

(72) Inventors: Jérôme Émile Georges Guillemont, Andé (FR); Tim Hugo Maria Jonckers, Heist-op-den-Berg (BE); Pierre Jean-Marie Bernard Raboisson, Wavre (BE); David Craig McGowan, Brussels (BE); Werner Constant Johan Embrechts, Beerse (BE); Bart Henri Theresia Stoops, Wechelderzande (BE); Florence Marie Herschke, Antwerp (BE); Jacques Armand Henri Bollekens, Ixelles (BE); Laurent Jacques Emile Calmus, Braine l'Alleud (BE)

(73) Assignee: Janssen Sciences Ireland Unlimited Company, Barnahely Ringaskidd (IE)

( * ) Notice: Subject to any disclaimer, the term of this patent is extended or adjusted under 35 U.S.C. 154(b) by 0 days.

(21) Appl. No.: 16/338,256

(22) PCT Filed: Sep. 28, 2017

(86) PCT No.: PCT/EP2017/074600
§ 371 (c)(1),
(2) Date: Mar. 29, 2019

(87) PCT Pub. No.: WO2018/060317
PCT Pub. Date: Apr. 5, 2018

(65) Prior Publication Data
US 2020/0031779 A1   Jan. 30, 2020

(30) Foreign Application Priority Data

Sep. 29, 2016   (EP) .................................... 16191568

(51) Int. Cl.
*C07D 239/48* (2006.01)
*C07F 9/6512* (2006.01)
*C07D 405/12* (2006.01)

(52) U.S. Cl.
CPC ......... *C07D 239/48* (2013.01); *C07D 405/12* (2013.01); *C07F 9/6512* (2013.01)

(58) Field of Classification Search
CPC .......... A61P 37/02; A61P 37/04; A61P 31/12; A61P 43/00; A61P 35/00; C07F 9/6512; C07D 405/12; C07D 239/48
USPC ........................................................ 514/86
See application file for complete search history.

(56) References Cited

U.S. PATENT DOCUMENTS

| | | | |
|---|---|---|---|
| 6,028,076 A | 2/2000 | Hirota et al. | |
| 6,329,381 B1 | 12/2001 | Kurimoto et al. | |
| 6,376,501 B1 | 4/2002 | Isobe et al. | |
| 6,458,798 B1 | 10/2002 | Fujita et al. | |
| 6,503,908 B1 | 1/2003 | Maw | |
| 6,583,148 B1 | 6/2003 | Kelley et al. | |
| 6,951,866 B2 | 10/2005 | Fujita et al. | |
| 7,030,118 B2 | 4/2006 | Lombardo et al. | |
| 7,091,232 B2 | 8/2006 | Chow et al. | |
| 7,498,409 B2 | 3/2009 | Vlach et al. | |
| 7,524,852 B2 | 4/2009 | Arai et al. | |
| 7,531,547 B2 | 5/2009 | Dillon et al. | |
| 7,754,728 B2 | 7/2010 | Isobe et al. | |
| 7,923,554 B2 | 4/2011 | Hoornaert et al. | |
| 8,012,964 B2 | 9/2011 | Kurimoto et al. | |
| 8,022,077 B2 | 9/2011 | Simmen et al. | |
| 8,455,458 B2 | 6/2013 | Marcum et al. | |
| 8,486,952 B2 | 7/2013 | Boy et al. | |
| 8,637,525 B2 | 1/2014 | Boy et al. | |
| 8,916,575 B2 | 12/2014 | McGowan et al. | |
| 9,133,192 B2 | 9/2015 | McGowan et al. | |
| 9,284,304 B2 | 3/2016 | McGowan et al. | |
| 9,365,571 B2 | 6/2016 | McGowan | |
| 9,376,448 B2 | 6/2016 | Charifson et al. | |
| 9,416,114 B2 | 8/2016 | Gembus et al. | |
| 9,422,250 B2* | 8/2016 | McGowan | A61K 31/506 |
| 9,499,549 B2 | 11/2016 | McGowan et al. | |
| 9,556,176 B2 | 1/2017 | Bonfanti et al. | |
| 9,556,199 B2 | 1/2017 | McGowan et al. | |
| 9,598,378 B2* | 3/2017 | McGowan | A61P 31/12 |
| 9,663,474 B2 | 5/2017 | Last | |
| 9,790,191 B2 | 10/2017 | McGowan et al. | |
| 9,878,996 B2 | 1/2018 | Silverman et al. | |
| 10,259,793 B2* | 4/2019 | McGowan | C07D 239/48 |

(Continued)

FOREIGN PATENT DOCUMENTS

CN   101784548 A   7/2010
EP   0882727   12/1998
(Continued)

OTHER PUBLICATIONS

Bekeredjian-Ding, et al., "T Cell-Independent, TLR-Induced IL-12p70 Production in Primary Human Monocytes", Journal of Immunology, vol. 176; pp. 7438-7446 (2006).

(Continued)

*Primary Examiner* — Tracy Vivlemore
*Assistant Examiner* — Ebenezer O Sackey
(74) *Attorney, Agent, or Firm* — Lathrop GPM LLP; Brian C. Trinque

(57) ABSTRACT

This invention relates to pyrimidine prodrug derivatives, processes for their preparation, pharmaceutical compositions, and their use in therapy.

13 Claims, No Drawings

(56) References Cited

U.S. PATENT DOCUMENTS

| | | | |
|---|---|---|---|
| 10,266,543 | B2 | 4/2019 | Bonfanti et al. |
| 10,272,085 | B2* | 4/2019 | McGowan ............ A61K 31/505 |
| 10,280,180 | B2 | 5/2019 | Bonfanti et al. |
| 10,377,738 | B2 | 8/2019 | McGowan et al. |
| 10,420,767 | B2* | 9/2019 | McGowan ............... A61P 31/12 |
| 2005/0054590 | A1 | 3/2005 | Averett |
| 2006/0258682 | A1 | 11/2006 | Liao et al. |
| 2007/0225303 | A1 | 9/2007 | Ogita et al. |
| 2008/0234251 | A1 | 9/2008 | Doherty |
| 2009/0285782 | A1 | 11/2009 | Gao et al. |
| 2010/0029585 | A1 | 2/2010 | Howbert |
| 2010/0143299 | A1 | 6/2010 | Gao et al. |
| 2014/0148433 | A1 | 5/2014 | Follmann et al. |
| 2015/0274676 | A1 | 10/2015 | McGowan et al. |
| 2015/0299221 | A1 | 10/2015 | Bonfanti et al. |
| 2015/0336907 | A1 | 11/2015 | Gembus et al. |
| 2016/0168150 | A1 | 6/2016 | McGowan et al. |
| 2016/0304531 | A1 | 10/2016 | Bonfanti et al. |
| 2019/0322678 | A1 | 10/2019 | Jonckers |

FOREIGN PATENT DOCUMENTS

| | | |
|---|---|---|
| EP | 0899263 A3 | 3/1999 |
| EP | 1552842 A1 | 6/2003 |
| EP | 1110951 A1 | 6/2006 |
| EP | 1939198 A1 | 7/2008 |
| EP | 1970373 A1 | 9/2008 |
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 2010522151 A | 7/2010 |
| JP | 2010532353 A | 10/2010 |
| WO | WO 199801448 A1 | 1/1998 |
| WO | WO 199808847 A1 | 3/1998 |
| WO | WO 199814448 A1 | 4/1998 |
| WO | WO 199850370 A1 | 11/1998 |
| WO | WO 1999028321 A1 | 6/1999 |
| WO | WO 199932122 A1 | 7/1999 |
| WO | WO 199940091 A1 | 8/1999 |
| WO | WO 199941253 A1 | 8/1999 |
| WO | WO 200006577 A1 | 2/2000 |
| WO | WO 200061562 A1 | 10/2000 |
| WO | WO 2002087513 A2 | 11/2002 |
| WO | WO 2002088080 A2 | 11/2002 |
| WO | WO 2003055890 A1 | 7/2003 |
| WO | WO 2004029054 A1 | 8/2004 |
| WO | WO 2005007672 A2 | 1/2005 |
| WO | WO 2005092892 A1 | 10/2005 |
| WO | WO 2005092893 A1 | 10/2005 |
| WO | WO 2006015985 A1 | 2/2006 |
| WO | WO 2006050843 A1 | 5/2006 |
| WO | WO 2006117670 A1 | 11/2006 |
| WO | WO 2006120252 A2 | 11/2006 |
| WO | WO 2007034881 A1 | 3/2007 |
| WO | WO 2007056208 A1 | 5/2007 |
| WO | WO 2007063934 A1 | 6/2007 |
| WO | WO 2007084413 A2 | 7/2007 |
| WO | WO 2007093901 A1 | 8/2007 |
| WO | WO 2008009078 A2 | 1/2008 |
| WO | WO 2008073785 A2 | 6/2008 |
| WO | WO 2008075103 A1 | 6/2008 |
| WO | WO 2008114008 A1 | 9/2008 |
| WO | WO 2008114817 A1 | 9/2008 |
| WO | WO 2008114819 A1 | 9/2008 |
| WO | WO 2008115319 A2 | 9/2008 |
| WO | WO 2008147697 A1 | 12/2008 |
| WO | WO 2009005687 A1 | 1/2009 |
| WO | WO 2009023179 A2 | 2/2009 |
| WO | WO 2009030998 A1 | 3/2009 |
| WO | WO 2009/067081 A1 | 5/2009 |
| WO | WO 2009080836 A2 | 7/2009 |
| WO | WO 2009099650 A2 | 8/2009 |
| WO | WO 2009032668 A3 | 9/2009 |
| WO | WO 2009134624 A1 | 11/2009 |
| WO | WO 2010006025 A1 | 1/2010 |
| WO | WO 2010007116 A2 | 1/2010 |
| WO | WO 2010133885 A1 | 11/2010 |
| WO | WO 2011014535 A1 | 2/2011 |
| WO | WO 2011049825 A1 | 4/2011 |
| WO | WO 2011049987 | 4/2011 |
| WO | WO 2011062253 A1 | 5/2011 |
| WO | WO 2011062372 A3 | 5/2011 |
| WO | 2012045089 A2 | 4/2012 |
| WO | WO 2012066335 A1 | 5/2012 |
| WO | WO 2012067269 A1 | 5/2012 |
| WO | 2012136834 A9 | 10/2012 |
| WO | WO 2012156498 A1 | 11/2012 |
| WO | WO 2013068438 A1 | 5/2013 |
| WO | WO 2013117615 A1 | 8/2013 |
| WO | 2014053516 A1 | 4/2014 |
| WO | 2014053595 A1 | 4/2014 |

OTHER PUBLICATIONS

Dowling, et al., "Toll-Like Receptors: the Swiss Army Knife of Immunity and Vaccine Development", Clinical & Translational Immunology, vol. 5; pp. e85 (1-10) (2016).
Guidotti, et al., "Viral Clearance Without Destruction of Infected Cells During Acute HBV Infection", Science, vol. 284; pp. 825-829(Apr. 30, 1999).
Isogawa, et al., "CD40 Activation Rescues Antiviral CD8+ T Cells from PD-1-Mediated Exhaustion", PLoS Pathogens, vol. 9(7); pp. e1003490 (1-16), (Jul. 2013).
Jo, et al., "Toll-Like Receptor 8 Agonist and Bacteria Trigger Potent Activation of Innate Immune Cells in Human Liver", PLoS Pathogens, vol. 10 (6); pp. e1004210 (1-13) (Jun. 2014).
Kurktschiev, et al., "Dysfunctional CD8+ T cells in Hepatitis B and C are Characterized by a Lack of Antigen-Specific T-bet Induction", J. Exp. Med., vol. 211(10); pp. 2047-2059 (2014).
Larange, et al., "Glucocorticoids Inhibit Dendritic Cell Maturation Induced by Toll-Like Receptor 7 and Toll-Like Receptor 8", Journal of Leukocyte Biology, vol. 91; pp. 105-117 (Jan. 2012).
McGowan, et al., "Novel Pyrimidine Toll-Like Receptor 7 and 8 Dual Agonists to Treat Hepatitis B Virus", Journal of Medicinal Chemistry, vol. 59 (17); pp. 7936-7949 ( 2016).
Northfelt et al., "A Phase I Dose-Finding Study of the Novel Toll-Like Receptor 8 Agonist VTX-2337 in Adult Subjects with Advanced Solid Tumors or Lymphoma", Clin Cancer Res, vol. 20 (14); pp. 3683-3691 (May 2014).
Paustian, et al., "Effect of Multiple Activation Stimuli on the Generation of TH1-polarizing Dendritic Cells", Human Immunology, vol. 72; pp. 24-31 (2011).
Schurich, et al., "The Third Signal Cytokine IL-12 Rescues the Anti-Viral Function of Exhausted HBV-Specific CD8 T Cells", PLoS Pathogens, vol. 9 (3); pp. e1003208 (1-12) (Mar. 2013).
Stephenson, et al., "TLR8 Stimulation Enhances Cetuximab-mediated Natural Killer Cell Lysis of Head and Neck Cancer Cells and Dendritic Cell Cross-priming of EGFR-specific CD8+ T Cells", Cancer Immunol Immunother, vol. 62; pp. 1347-1357 (2013).
Thimme, et al., "CD8+ T Cells Mediate Viral Clearance and Disease Pathogenesis during Acute Hepatitis B Virus Infection", Journal of Virology, vol. 77 (1); pp. 68-76 (Jan. 2003).
U.S. Appl. No. 14/110,054, filed Oct. 4, 2013, David McGowan, 2014-0045849, Feb. 13, 2014, U.S. Pat. No. 9,422,250, Aug. 23, 2016.
U.S. Appl. No. 15/209,637, filed Jul. 13, 2016, David McGowan, 2017/0239245, Aug. 24, 2017, U.S. Pat. No. 10,272,085, Apr. 30, 2019.
U.S. Appl. No. 15/867,041, filed Jan. 10, 2018, David McGowan, 2018/0207155, Jul. 26, 2018.
U.S. Appl. No. 16/530,385, filed Aug. 2, 2019, David McGowan.
U.S. Appl. No. 14/118,527, filed Nov. 18, 2013, David McGowan, 2014/0073642, Mar. 13, 2014, U.S. Pat. No. 8,916,575, Dec. 23, 2014.

(56) References Cited

OTHER PUBLICATIONS

U.S. Appl. No. 15/420,045, filed Jan. 30, 2017, Jean-Francois Bonfanti, 2017/0283419, Oct. 5, 2017, U.S. Pat. No. 10,280,167, May 7, 2019.
U.S. Appl. No. 14/357,495, filed May 9, 2014, Jean-Francois Bonfanti, 2014/0323441, Oct. 30, 2014, U.S. Pat. No. 9,556,176, Jan. 31, 2017.
U.S. Appl. No. 16/404,601, filed May 6, 2019, Jean-Francois Bonfanti.
U.S. Appl. No. 14/377,064, filed Aug. 6, 2014, David McGowan, 2014/0350031, Nov. 27, 2014, U.S. Pat. No. 9,133,192, Sep. 15, 2015.
U.S. Appl. No. 14/818,094, filed Aug. 4, 2015, David McGowan, 2015/0336955, Nov. 26, 2015, U.S. Pat. No. 9,365,571, Jun. 14, 2016.
U.S. Appl. No. 14/408,681, filed Dec. 17, 2014, Jean-Francois Bonfanti, 2015/0299221, Oct. 22, 2015, U.S. Pat. No. 10,280,180, May 7, 2019.
U.S. Appl. No. 16/404,638, filed May 6, 2019, Jean-Francois Bonfanti.
U.S. Appl. No. 14/420,066, filed Feb. 6, 2015, David McGowan, 2015/0239872, Aug. 27, 2015, U.S. Pat. No. 9,284,304, Mar. 15, 2016.
U.S. Appl. No. 14/434,021, filed Apr. 7, 2015, David McGowan, 2015/0239892, Aug. 27, 2015, U.S. Pat. No. 9,499,549, Nov. 22, 2016.
U.S. Appl. No. 15/333,947, filed Oct. 25, 2016, David McGowan, 2017/0044169, Feb. 16, 2017, U.S. Pat. No. 10,259,814, Apr. 16, 2019.
U.S. Appl. No. 16/382,727, filed Apr. 12, 2019, David McGowan.
U.S. Appl. No. 14/432,269, filed Mar. 30, 2015, Vincent Gembus, 2015/0336907, Nov. 26, 2015, U.S. Pat. No. 9,416,114, Aug. 16, 2016.
U.S. Appl. No. 14/431,973, filed Mar. 27, 2015, David McGowan, 2015-0274676, Oct. 1, 2015, U.S. Pat. No. 9,790,191, Oct. 17, 2017.
U.S. Appl. No. 14/443,305, filed May 15, 2015, Stefaan Julien Last, 2015/0284339, Oct. 8, 2015, U.S. Pat. No. 9,663,474, May 30, 2017.
U.S. Appl. No. 15/591,473, filed May 10, 2017, Stefaan Julien Last, 2017/0349557, Dec. 7, 2017, U.S. Pat. No. 10,253,003, Apr. 9, 2019.
U.S. Appl. No. 16/377,752, filed Apr. 8, 2019, Stefaan Julien Last.
U.S. Appl. No. 14/769,773, filed Aug. 21, 2015, David McGowan, 2015/0376140, Dec. 31, 2015, U.S. Pat. No. 9,598,378, Mar. 21, 2017.
U.S. Appl. No. 15/464,050, filed Mar. 20, 2017, David McGowan, 2017/0342035, Nov. 30, 2017, U.S. Pat. No. 10,259,793, Apr. 16, 2019.
U.S. Appl. No. 16/382,816, filed Apr. 12, 2019, David McGowan.
U.S. Appl. No. 14/781,291, filed Sep. 29, 2015, Jean-Francois Bonfanti, 2016/0304531, Oct. 20, 2016, U.S. Pat. No. 10,266,543, Apr. 23, 2019.
U.S. Appl. No. 16/389,751, filed Apr. 19, 2019, Jean-Francois Bonfanti.
U.S. Appl. No. 14/892,701, filed Nov. 20, 2015, David McGowan, 2016/0108021, Apr. 21, 2016, U.S. Pat. No. 10,377,738, Aug. 13, 2019.
U.S. Appl. No. 16/432,423, filed Jun. 5, 2019, David McGowan.
U.S. Appl. No. 14/392,214, filed Dec. 23, 2018, David McGowan, 2016-0168150, Jun. 16, 2016, U.S. Pat. No. 10,385,054, Aug. 20, 2019.
U.S. Appl. No. 16/441,213, filed Jun. 14, 2019, David McGowan.
U.S. Appl. No. 14/908,237, filed Jan. 28, 2016, David McGowan, 2016/0168164, Jun. 16, 2016, U.S. Pat. No. 9,556,199, Jan. 31, 2017.
U.S. Appl. No. 15/420,055, filed Jan. 30, 2017, David McGowan, 2017/0298079, Oct. 19, 2017, U.S. Pat. No. 10,316,043, Jun. 11, 2019.
U.S. Appl. No. 16/405,518, filed May 7, 2019, David McGowan.

U.S. Appl. No. 16/312,687, filed Dec. 21, 2018, Tim Hugo Maria Jonckers.
Abdillahi, et al., "Synthesis of a Novel Series of Thieno[3,2-d]pyrimidin-4-(3H)-ones", Synthesis, vol. 9: pp. 1428-1430 (2010).
Banker (Editor), "Prodrugs", Modern Pharmaceutics, Third Edition: pp. 596 (1976).
Barker, et al., "A Rapid Conversion of 3-Oxothiolanes into 3-Aminothiophenes", Synthetic Communications, vol. 32(16): pp. 2565-2568 (2002).
Bennet, et al. (Editor), "Part XIV Oncology", Cecil Textbook of Medicine, vol. 1, 20th Edition: pp. 1004-1010 (1996).
Brittain, et al., "Effects of Pharmaceutical Processing on Drug Polymorphs and Solvates", Polymorphism in Pharmaceutical Solids, 1999, pp. 331-360, Chapter 8.
Bruns, et al, "Solubilities of Adenosine Antagonists Determined by Radioreceptor Assay", Journal of Pharmacy and Pharmacology, vol. 41: pp. 590-594 (1989).
Chawla, et al., "Challenges in Polymorphism of Pharmaceuticals", Current Research & Information on Pharmaceutical Sciences, vol. 5(1): pp. 9-12 (Jan.-Mar. 2004).
De Clercq, et al., "(S)-9-(2,3-Dihydroxypropyl)adenine: An Aliphatic Nucleoside Analaog with Broad-Spectrum Antiviral Activity", Science, 1978, pp. 563-565, vol. 200.
De Nardo, "Toll-Like Receptors: Activation, Signalling and Transcriptional Modulation", Cytokine, 2015, pp. 181-189, vol. 74.
Dermer, "Another Anniversary for the War on Cancer", Bio/Technology, vol. 12: pp. 320 (Mar. 1994).
Douglas, Jr., "Introduction of Viral Diseases", Cecil Textbook of Medicine, 20th Edition, vol. 2: pp. 1973-42 (1996).
Freshney, et al., "Culture of Animal Cells", Manual of Basic Technique, 1983, pp. 1-6. Chapter 1.
Fried, et al., "Peginterferon Alfa-2a Plus Ribavirin for Chronic Hepatitis C Virus Infection", New England Journal of Medicine, Sep. 26, 2002, pp. 975-985, vol. 347 (13).
Grimm, et al., "Toll-like receptor (TLR) 7 and TLR8 expression on CD133+ cells in colorectal cancer points to a specific rold for inflammation inducted TLRs in tumourigenesis and tumour progression", European Journal of Cancer, 2010, pp. 2849-2857, vol. 46.
Hackam, et al, "Translation of Research Evidence From animals to Humans", JAMA, vol. 296 (14): pp. 1731-1732 (2006).
Hood, et al., "Immunoprofiling toll-like receptor ligands Comparison of Immunostimulatory and proinflammatory profiles in ex vivo human blood models", Human Vaccines, vol. 6(4): pp. 322-335 (Apr. 2010).
Horscroft, et al., "Antiviral applications of toll-like receptor agonists", J. Antimicrob. Chemother., pp. 1-13 (Jan. 18, 2016).
Huddleston, et al., "A Convenient Synthesis of 2-Substituted 3-Hydroxy-And 3-Amino-Thiophens From Derivatives of 2-Choroacrylic Acid", Synthetic Communications, vol. 9(8): pp. 731-734 (1979).
Isobe, et al., "Synthesis and Structure—Activity Relationships of 2-Substituted-8-hydroxyadenine Derivatives as Orally Available Interferon Inducers without Emetic Side Effects", Bioorganic & Medicinal Chemistry, vol. 11: pp. 3641-3647, (2003).
Jiang, et al., "Synthesis of 4-chlorothieno[3,2-d]pyrimidine", Chemical Industry and Engineering Progress, vol. 30: pp. 2532-2535, (2011). [With English Abstract].
Jordan, "Tamoxifen: A Most Unlikely Pioneering Medicine", Nature Reviews, vol. 2: pp. 205-213, (Mar. 2003).
Kanzler, et al., "Therapeutic Targeting of Innate Immunity with Toll-Like Receptor Agonists and Antagonists", Nature Medicine, vol. 13(5): pp. 552-559 (May 2007).
Krieger, et al, Enhancement of Hepatitis C Virus RNA Replication by Cell Culture, Journal of Virology, May 1, 2001, 4614-1624, 75-10, DE.
Kurimoto, et al., "Synthesis and Structure—Activity Relationships of 2-Amino-8-hydroxyadenines as Orally Active Interferon Inducing Agents", Bioorganic & Medicinal Chemistry, vol. 11: pp. 5501-5508 (2003).
Liu, et al., "Synthesis and Biological Activity of 3-and 5-Amino Derivatives of Pyridine-2Carboxaldehyde Thiosemicarbazone", J. Med. Chem, Vo. 39: pp. 2586-2593 (1996).

(56) References Cited

OTHER PUBLICATIONS

Lohmann et al, Viral and Cellular Determinants of Hepatitis C Virus RNA Replication in Cell Culture, Journal of Virology, vol. 77(5): pp. 3007-3019 (Mar. 2003).
Lohmann, et al., Replication of Subgenomic Hepatitis C Virus RNAs in a Hepatoma Cell Line, Science, 1999, pp. 110-113, vol. 285.
Makkouk et al., "The potential use of Toll-Like Receptors (TLR) agonistd and antagonists as prophylactic and/or therapeutic agents", Immunopharmacology and Immunotoxicology, vol. 31(3): pp. 331-338 (2009).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).
Musmuca, et al, "Small-Molecule interferon Inducers. Toward the Comprehension of the Molecular Determinants through Ligand-Based Approaches",,J. Chem. Inf. Model., vol. 49: pp. 1777-1786 (2009).
Newman, et al., "Solid-State Analysis of the Active Pharmaceutical Ingredient in Drug Products", Drug Discovery Today, Oct. 19, 2003, pp. 898-905, vol. 8(19).
O'Hara, et al., "Regioselective Synthesis of Imidazo[4,5-g]quinazoline Quinone Nucleosides and Quinazoline Amino Nucleosides. Studies of their Xanthine Oxidase and Purine Nucleoside Phosphorylase Substrate Activity", J. Org. Chem. vol. 56: pp. 776-785 (1991).
Ohto, et al., "Structure and Function of Toll-Like Receptor 8", Microbes and Infections, vol. 16: pp. 273-282 (2014).
Thomas, et al., "Investigating Toll-Like Receptor Agonists for Potential to Treat Hepatitis C Virus Infection", Antimicrobial Agents and Chemotherapy, vol. 51(8): pp. 2969-2978 (Aug. 2007).
Tran, et al, "Design and optimization of orally active TLR7 agonists for the treatment of hepatitis C virus infection", Bioorganic & Medicinal Chemistry Letters, vol. 21: pp. 2389-2393 (2011).
Ulrich, et al, "Crystallization", Kirk-Othmer Encyclopedia of Chemical Technology, Chapter 4: pp. 1-63, (Aug. 16, 2002).
Vedantham, et al., "Mechanism of Interferon Action in Hairy Cell Leukemia: a Model of Effective Cancer Biotherapy", Cancer Research, vol. 52: pp. 1056-1066 (Mar. 1, 1992).
Vippagunta, et al., "Crystalline Solids", Advance Drug Delivery Reviews, vol. 48: pp. 3-26 (2001).
Warshakoon, et al., "Potential Adjuvantic Properties of Innate Immune Stimuli", Human Vaccines, vol. 5(6): pp. 381-394 (Jun. 2009).
Wermuth, "Molecular Variations Based on Isosteric Replacements", The Practice of Medicinal Chemistry, 1996, pp. 203-237, Ch. 13.
Wolff, et al, Burger's Medicinal Chemistry and Drug Discovery, -, 1994, pp. 975-977, 5th Edition, vol. 1.
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Yu, et al, "Toll-Like Receptor 7 Agonists: Chemical Feature Based", PLoS One, vol. 8 (3): pp. 1-11 e56514, (Mar. 20, 2013).
Yu, et al., "Dual Character of Toll-Like Receptor Signaling: Pro-Tumorigenic Effects and Anti-Tumor Functions", Biochimica et Biophysica Acta, vol. 1835: pp. 144-154 (2013).
Zhao, et al., "Toll-Like Receptors and Prostate Cancer", Frontiers in Immunology, vol. 5 (Article 352): pp. 1-7 (Jul. 2014).
Bizanek, et al., Isolation and Structure of an Intrastrand Cross-Link Adduct of Mitomycin C nd DNA, Biochemistry, 1992, pp. 3084-3091, vol. 31.
Organic Syntheses Collective, "3-Methylcoumarone", Organic Syntheses Collective, 1963; pp. 43-46, vol. 4.
Tomonori, et al., "Ti-Crossed-Claisen Condensation between Carboxylic Ester and Acid Chlorides or Acids: a Highly Selective and General Method for the Preparation of Various β-Keto Esters", Journal of the American Chemical Society, vol. 127:pp. 2854-2855 (2005).
Isobe, et al., "Synthesis and Biological Evaluation of Novel 9-Substituted-8-Hydroxyadenine Derivatives as Potent Inferferon Inducers", J. Med. Chem., vol. 49; pp. 2088-2095 (2006).
Jurk, et al., "Human TLR7 or TLR8 Independently Confer Responsiveness to the Antiviral Compound R-848", Nature Immunology, Jun. 2002, pp. 499, vol. 3 (6).
Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).
Lee, et al., "Activation of Anti-Hepatitis C Virus Responses via Toll-Like Receptor 7", PNAS, vol. 3 (6); pp. 1828-1833 (Feb. 7, 2006).
Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).
Baraldi, P., et al., "New Strategies for the Synthesis of A3 Adenosine Receptor Antagonists", Bioorganic & Medicinal Chemistry, vol. 11, pp. 4161-4169 (2003).
Bell, L., et al., "Chemistry of 5-Pyrimidinecarboxaldehydes", J. Heterocyclic Chemistry, vol. 29, pp. 41-44 (2003).
Hoffmann, Jules A., The Immune Response of *Drosophila*: Nature, vol. 426, pp. 33-38 (2003).
Mesguiche, V., et al., "4-Alkoxy-2,6-diaminopyrimidine Derivatives: Inhibitors of Cyclin Dependent Kinases 1 and 2", Bioorganic & Medicinal Chemistry Letters, vol. 13, pp. 217-222 (2003).
Takeda, K., et al.; "Toll-Like Receptors", Annual Rev. Immunology, vol. 21, pp. 335-376 (2003).
International Search Report dated Jul. 15, 2014 for Application No. PCT/EP2014/060603.
International Search Report for Application No. PCT/EP2012/059234, dated Nov. 18, 2013.
International Search Report for Application No. PCT/EP2012/072090, dated Jan. 4, 2013.
International Search Report for Application No. PCT/EP2013/052372, dated Apr. 17, 2013.
International Search Report for Application No. PCT/EP2013/064763, dated Aug. 3, 2013.
International Search Report for Application No. PCT/EP2013/066673, dated Sep. 6, 2013.
International Search Report for Application No. PCT/EP2013/070990, dated Jan. 17, 2014.
International Search Report for Application No. PCT/EP2013/070488, dated Nov. 14, 2013.
International Search Report for Application No. PCT/EP2013/073901, dated Dec. 16, 2013.
International Search Report for Application No. PCT/EP2014/053273, dated Mar. 18, 2014.
International Search Report for Application No. PCT/EP2014/056270, dated Jul. 21, 2014.
International Search Report for Application No. PCT/EP2014/063467, dated Nov. 3, 2014.
International Search Report for Application No. PCT/EP2014/066219, dated Nov. 13, 2014.
International Search Report for Application No. PCT/EP2012/056388, dated May 31, 2012.

\* cited by examiner

PYRIMIDINE PRODRUGS FOR THE TREATMENT OF VIRAL INFECTIONS AND FURTHER DISEASES

CROSS-REFERENCE TO RELATED APPLICATIONS

This application is a national phase entry of International Application No. PCT/EP2017/074600, filed on Sep. 28, 2019, which claims priority to EP Patent Application No. 16191568.1, filed Sep. 29, 2016, each of which is incorporated herein in its entirety.

The present invention relates to pyrimidine prodrug derivatives and the use of said pyrimidine prodrug derivatives in the treatment of viral infections, immune disorders, and cancer, or as a vaccine adjuvant, whereby the induction of a T helper 1 (Th1) immune response is desired.

For instance, in the treatment of chronic hepatitis B (HBV), a Th1 response to reinvigorate exhausted virus-specific CD8+ T cells in the infected organs would be highly beneficial (*Science* 1999, 284, 825-829; *J. Virol.* 2003, 77, 68-76). Such a response is induced by the innate immune system, in particular by stimulating Toll-like receptors (TLR) such as TLR3, 4, 7, 8 and 9 (*Clin. Transl. Immunol.* 2016, 5(5):e85). TLR8 agonists induce one of the strongest Th1 response in human cells, via the secretion of IL-12p70 and the upregulation of CD40 or OX40L activation markers and indirectly IFNγ (*J Immunol.* 2006, 176(12):7438-46; *Hum Immunol.* 2011 January; 72(1):24-31; *J Leukoc Biol.* 2012, 91(1):105-17), which have shown their potential ex vivo to treat chronic HBV (*PLoS Pathog.* 2013, 9, e1003208; *J. Exp. Med.* 2014, 211, 2047-2059; *PLoS Path.* 2013, 9, e1003490; *PLoS Pathog.* 2014, 10, e1004210).

Only one TLR8 agonist, administered by subcutaneous injection, is currently in development for cancer indications (*Clin. Cancer Res.* 2014, 20, 3683; *Cancer Immunol. Immunother.* 2013, 62, 1347; WO2012/045089. See also US20080234251, US20100029585). Therefore, there exists a strong need for orally-available TLR8 agonists to treat infections such as chronic HBV.

In accordance with the present invention a compound of formula (I) is provided

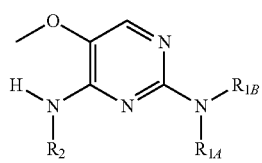

or a pharmaceutically acceptable salt, solvate or polymorph thereof, wherein $R_{1A}$ is selected from hydrogen, a substituted or unsubstituted $C_{1-3}$ alkyl, heterocycle, or a substituted or unsubstituted phosphoramidate, $R_{1B}$ is selected from hydrogen, a substituted or unsubstituted $C_{1-3}$ alkyl, heterocycle, or a substituted or unsubstituted phosphoramidate, with the exception that $R_{1A}$ and $R_{1B}$ are not both hydrogen, $R_2$ is a $C_{1-8}$ alkyl, which is optionally substituted by a hydroxyl group.

The present invention concerns a prodrug composition of a pharmaceutical compound. The pharmaceutical compound is characterized by bioavailability of 50% or less and a molecular weight in the range of 100-1000 Daltons. Also described is a method of delivering a pharmaceutical compound to an individual including the step of orally administering said prodrug to an individual. The prodrug moiety is attached to the pharmaceutical compound wherein the modification allows the TLR8 agonist potential to be attenuated. The prodrug is enzymatically cleaved prior to or at the site of the liver to yield the pharmaceutical compound, such that the pharmaceutical compound is delivered to the individual limiting TLR8 agonism prior to the liver.

In a first embodiment the present invention provides compounds of formula (I) wherein $R_{1A}$ and/or $R_{1B}$ are a substituted or unsubstituted phosphoramidate and wherein $R_2$ is a $C_{1-6}$ alkyl preferably substituted by a hydroxyl group.

In a second embodiment the present invention provides compounds of formula (I) wherein $R_{1A}$ and/or $R_{1B}$ are methyl and wherein $R_2$ is a $C_6$-alkyl substituted by a hydroxyl group.

The compounds of formula (I) in any stereochemical form and their pharmaceutically acceptable salt, solvate or polymorph thereof have activity as pharmaceuticals, in particular as inducers of interferon.

So, in a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of a disorder in which the induction of interferon is involved.

The term "alkyl" refers to a straight-chain or branched-chain saturated aliphatic hydrocarbon containing the specified number of carbon atoms.

"Heterocycle" refers to molecules that are saturated or partially saturated and include tetrahydrofuran, tetrahydropyran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

EXPERIMENTAL SECTION

Preparation of 2 and 3

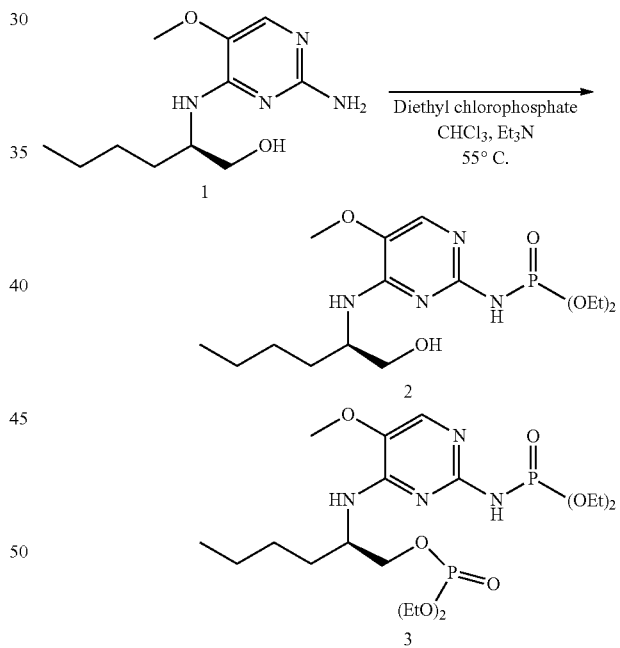

In a closed vessel, diethyl chlorophosphate (0.3 mL, 2.08 mmol) was added dropwise to a suspension of 1 (For synthesis of 1 see WO2012/136834)(0.5 g, 2.08 mmol) in CHCl$_3$ (20 mL) at room temperature for 5 min, and then Et$_3$N (0.38 mL, 2.71 mmol) was added dropwise. The reaction mixture was heated to 55° C. The solvent was removed under reduced pressure. The crude was purified by reverse phase chromatography. First purification (start 95% [0.1% HCOOH]-5% [CH$_3$CN:CH$_3$OH 1:1] and finished 0% [0.1% HCOOH]-100% [CH$_3$CN:CH$_3$OH 1:1). Second purification (start 81% [25 mM NH$_4$HCO$_3$]-19%[100% CH$_3$CN] and finished 45% [25 mM NH$_4$HCO$_3$]-55% [100%

CH$_3$CN]. The best fractions were pooled and the solvents removed to afford compounds:

2, LC-MS ES$^+$ m/z=377.1; Rt. 2.01 min, method A. [α]$_D^{23}$+7.6 (c 0.64, MeOH). mp 161.4° C. $^1$H NMR (300 MHz, CD$_3$OD) δ ppm 0.91 (m, 3H), 1.26-1.43 (m, 10H), 1.57 (m, 1H), 1.67 (m, 1H), 3.60 (d, J=5.1 Hz, 2H), 3.82 (s, 3H), 4.13 (m, 4H), 4.24 (m, 1H), 7.41 (s, 1H).

3, LC-MS ES$^+$ m/z=513.0; Rt. 2.49 min, method A. [α]D$^{23}$+32.1 (c 0.29, MeOH). $^1$H NMR (300 MHz, CD$_3$OD) δ ppm 0.91 (m, 3H), 1.22-1.44 (m, 16H), 1.68 (m, 2H), 3.83 (s, 3H), 3.98-4.24 (m, 10H), 4.41 (m, 1H), 7.46 (s, 1H).

Preparation of 5

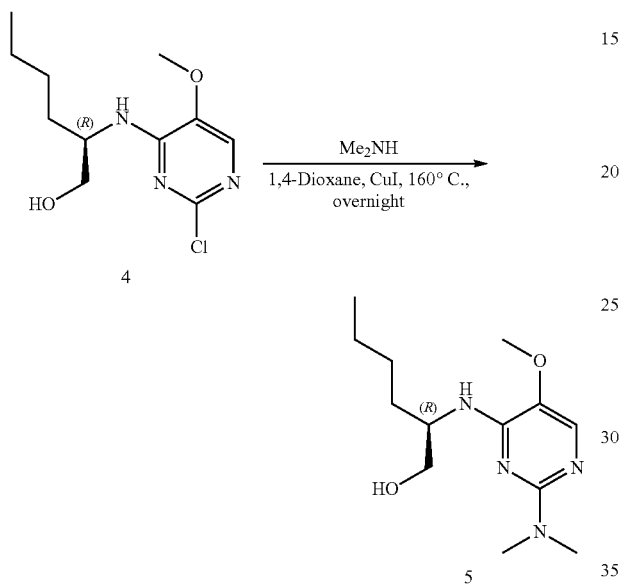

An aqueous solution of dimethylamine (6.67 mL, 132.8 mmol) and copper (I) iodide (19.28 mg, 0.13 mmol) were added to a solution of (R)-2-((2-chloro-5-methoxy-pyrimidin-4-yl)amino)hexan-1-ol (For synthesis see WO2012/136834) (500 mg, 1.92 mmol) in 1,4-dioxane (5 mL) in a steel reactor. The reaction mixture was heated to 160° C. overnight. The reaction was cooled and filtered through packed Celite and the solvent was evaporated to dryness to give a crude that was purified by column chromatography on silica gel to yield (R)-2-((2-(dimethylamino)-5-methoxypyrimidin-4-yl)amino)hexan-1-ol (250 mg, 0.93 mol). LC-MS ES$^+$ m/z=269.1; Rt: 2.00 min, method A. $^1$H NMR (300 MHz, CD$_3$OD) δ 0.90 (m, 3H), 1.25-1.47 (m, 4H), 1.58 (m, 1H), 1.67 (m, 1H), 3.05 (s, 6H), 3.61 (m, 2H), 3.77 (s, 3H), 4.21 (m, 1H), 7.35 (br s, 1H). [α]$^{23}$−8.25 (c 0.64, CH$_3$OH). mp 86.1° C.

Preparation of 6

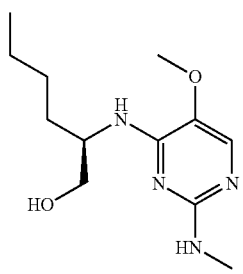 [SMILES: CCCC[C@H](CO)Nc1nc(NC)ncc1OC]

Compound 6 was prepared analogous to the procedure to prepare 5 with the exception that methylamine was used. LC-MS ES$^+$ m/z=255.1; Rt: 1.85 min, method A. $^1$H NMR (300 MHz, CD$_3$OD) δ ppm 0.91 (m, 3H), 1.26-1.44 (m, 4H), 1.56 (m, 1H), 1.66 (m, 1H), 2.81 (s, 3H), 3.60 (m, 2H), 3.76 (s, 3H), 4.18 (m, 1H), 7.32 (br s, 1H). [α]D$^{23}$+1.8 (c 0.59, CH$_3$OH). mp 86.1° C.

Preparation of 8

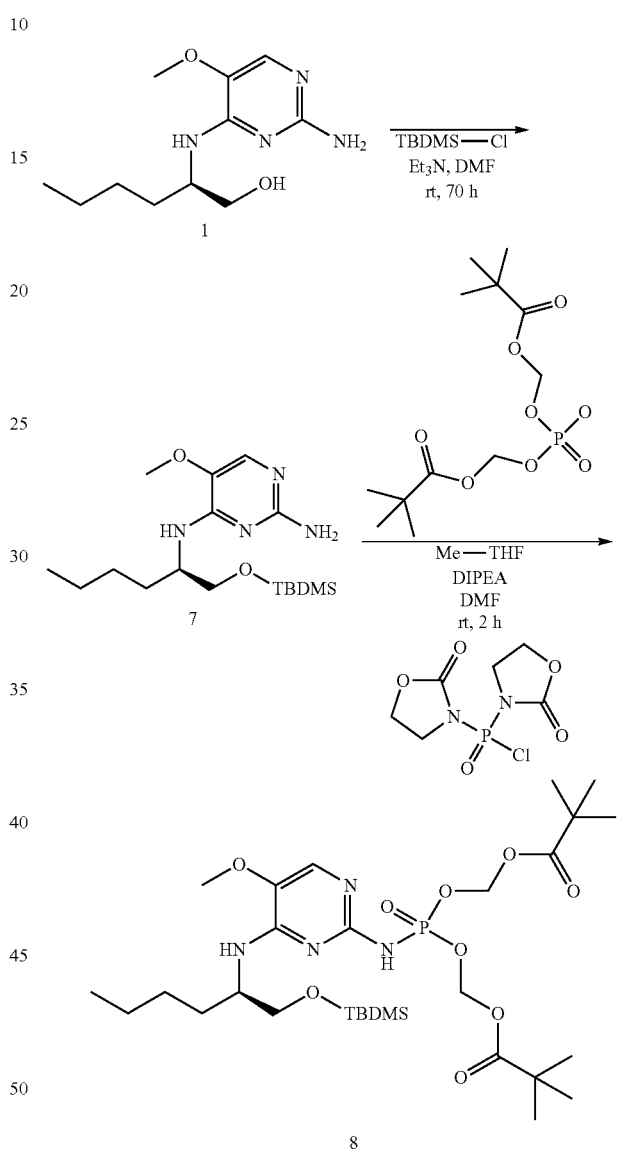

Step 1. Preparation of 7. TBDMSCI (7.53 g, 49.9 mmol) was added to a solution of 1 (10.0 g, 41.6 mmol) and Et$_3$N (11.6 mL, 83.2 mmol) in DMF (120 mL). The mixture was stirred at rt for 70 h. EtOAc and a 10% aq. NaHCO$_3$ was poured into the solution. The layers were separated and the organic layer was washed with brine (twice). The organic layer was dried over MgSO$_4$, the solids were removed by filtration, and the solvent of the filtrate was removed under reduced pressure to give an orange oil, purified by silica column chromatography using the following gradient: from CH$_2$Cl$_2$ 100% to 90%, CH$_3$OH 0 to 10% (with 5% aq. NH$_3$) to afford 7, as a colorless oil. $^1$H NMR (400 MHz, DMSO-d$_6$) δ ppm 0.01 (s, 6H), 0.80-0.88 (m, 12H), 1.17-1.34 (m, 4H), 1.45 (m, 1H), 1.61 (m, 1H), 2.48-2.52 (m, 12H), 3.49 (dd, J=10.00, 6.50 Hz, 1H), 3.58 (dd, J=10.00, 4.70 Hz), 3.66 (s, 3H), 4.09 (m, 1H), 5.44 (s, 2H), 5.84 (d, J=9.09 Hz, 1H), 7.37 (s, 1H). LC-MS ES+ m/z=355.1, Rt: 3.76, Method: B). $[\alpha]_D^{20}$+53.33 (c 0.3, DMF).

Step 2. Under $N_2$, bis(2-oxo-3-oxazolidinyl)phosphinic chloride (1.05 g, 4.11 mmol) was added portionwise to a solution of ((hydroxyphosphoryl)bis(oxy))bis(methylene) bis(2,2-dimethylpropanoate) (1.61 g, 4.93 mmol) and DIPEA (2.83 mL, 16.4 mmol) in anhydrous 2-methyltetrahydrofuran/DMF (20 mL/14.5 mL). The mixture was stirred at rt for 2 h.

Step 3. Then 7 (729 mg, 2.06 mmol) in anhydrous 2-methyltetrahydrofuran (17 mL) was added and the mixture was stirred at rt for 2 h. The reaction mixture was diluted with EtOAc and water, the organic layer was washed with brine (twice), dried over $MgSO_4$, the solids were removed by filtration, and the solvent of the filtrate was removed under reduced pressure, then purified by silica column chromatography using a mobile phase gradient: from heptane/EtOAc (80/20 to 0/100) to give 290 mg of 8 as a colorless oil. $^1$H NMR (400 MHz, DMSO-$d_6$) δ ppm 0.84 (t, J=6.82 Hz, 3H), 1.12 (s, 18H), 1.18-1.34 (m, 4H), 1.41-1.65 (m, 2H), 3.42 (m, 2H), 3.74 (s, 3H), 4.03 (m, 1H), 4.61 (t, J=5.56 Hz, 1H), 5.60 (m, 4H), 6.44 (s, 1H), 7.45 (s, 1H), 8.77 (m, 1H). LC-MS ES+ m/z=547.6, Rt: 3.02, Method: B Preparation of (2R)-2-((5-methoxy-2-((tetrahydrofuran-2-yl)amino)pyrimidin-4-yl)-amino)hexan-1-ol (9)

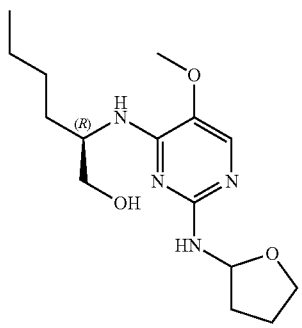

In a Schlenk flask, DOWEX® 50WX2 (100-200 mesh) resin (one spatula) was added at room temperature to a mixture of 1 (4 g, 11.3 mmol), 2,3-dihydrofuran (1031 μL, 13.5 mmol, 1.2 eq.) in anhydrous dichloroethane (99 mL). The mixture was stirred at 80° C. for 20 h. Additional 2,3-dihydrofuran (688 μL, 9.03 mmol, 0.8 eq.) was added and the mixture was stirred at 80° C. for 20 h. An extraction was performed with $CH_2Cl_2$ and water, and the layers were separated. The organic layer was dried over $MgSO_4$, filtered, and the solvent was removed under reduced pressure to afford the titled compound.

$^1$H NMR (400 MHz, DMSO-$d_6$) δ ppm 0.84 (t, J=6.57 Hz, 3H), 1.18-1.33 (m, 4H), 1.46 (m, 1H), 1.58 (m, 1H), 1.74 (m, 2H), 1.96 (m, 2H), 3.41 (m, 2H), 3.61 (m, 1H), 3.64-3.73 (m, 4H), 4.04 (m, 1H), 4.65 (t, J=5.31 Hz, 1H), 5.73 (m, 1H), 6.00 (d, J=9.09 Hz, 1H), 6.54 (m, 1H), 7.42 (s, 1H). LC-MS ES+ m/z=311.3, Rt: 2.30, Method: B)

Preparation of (2R)-2-((5-methoxy-2-((tetrahydro-2H-pyran-2-yl)amino)pyrimidin-4-yl)-amino)hexan-1-ol (10)

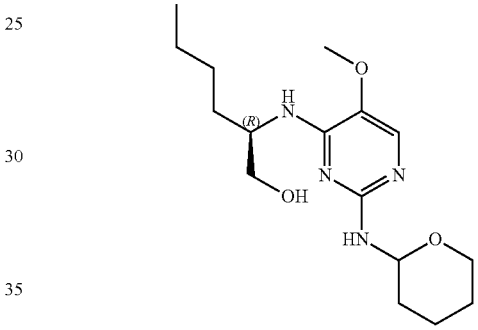

Compound 10 was prepared according to the procedure to prepare 9, with the exception that 3,4-dihydro-2H-pyran was used.

$^1$H NMR (400 MHz, DMSO-$d_6$) δ ppm 0.85 (m, 3H), 1.17-1.66 (m, 12H), 1.82 (br d, J=4.55 Hz, 1H), 3.35-3.50 (m, 3H), 3.70 (s, 3H), 3.77 (m, 1H), 4.02 (m, 1H), 4.66 (m, 1H), 5.01 (m, 1H), 6.02 (d, J=8.59 Hz, 1H), 6.46 (t, J=10.11 Hz, 1H), 7.43 (m, 1H). LC-MS ES+ m/z=325.1, Rt: 2.45, Method: B)

Analytical Methods.

| Method code | Instrument | Column | Mobile phase | Gradient | Flow (mL/min) / Col T(° C.) | Run time (min) |
|---|---|---|---|---|---|---|
| A | Agilent 1100-DAD-MSD G1956A | YMC-pack ODS-AQ C18 (50 × 4.6 mm, 3 μm) | A: 0.1% HCOOH in $H_2O$ B: $CH_3CN$ | From 95% A to 5% A in 4.8 min, held for 1.0 min, to 95% A in 0.2 min. | 2.6 / 35 | 6.0 |
| B | Waters Acquity | BEH C18 (1.7 μm, 2.1 × 100 mm) | A: 95% 7 mM $NH_4OAc$/5% $CH_3CN$ B: $CH_3CN$ | From 84.2% A and 15.8% B (hold for 0.49 min) to 10.5% A and 89.5% B in 2.18 min, hold for 1.94 min, and back to the initial | 0.343 / 40 | 6.07 |

-continued

| Method code | Instrument | Column | Mobile phase | Gradient | Flow (mL/min) Col T(° C.) | Run time (min) |
|---|---|---|---|---|---|---|
| | | | | conditions in 0.73 min, hold for 0.73 min | | |

Supporting ADME data.

Intrinsic clearance ($CL_{int}$). $CL_{int}$ was determined in rat and human liver microsomes. Incubations were performed at 37° C., at a concentration of 1 µM of compound, and a microsomal protein concentration of 1 mg/mL. Serial samples were removed at intervals of up to 60 min and analyzed for the concentration of compound to determine its intrinsic clearance rate. Compound was incubated in rat and human hepatocytes ($10^6$ cells/mL) at 1 µM for 0, 10, 20, 40, 60 and 120 min. Serial samples were removed at intervals of up to 120 min and analyzed for the concentration of compound to determine its intrinsic clearance rate.

Permeability and Efflux in vitro. The in vitro permeability and potential to be transported by P-glycoprotein (P-gp) was determined using an MDCK cell line transfected with human MDR1 (P-glycoprotein). Compound was added to the apical (A) or basolateral (B) side of a confluent monolayer of MDCK-MDR1 cells. Permeability in the A→B direction in absence and presence of GF120918 and in the B→A direction in absence of GF120918 was measured by monitoring the appearance of the test compound on the opposite side of the membrane using a specific LC-MS/MS method. The efflux ratio (B→A-GF120918/A→B-GF120918) was calculated to determine whether the test compound was a P-gp substrate.

Plasma stability. Plasma stability is measured in rat and human plasma for 7 or 24 h at 37° C. Compounds are incubated at 1 µM. Incubations are performed manually in a 24-well plate and serial samples (100 µL) are removed at various time points prior to quenching with acetonitrile.

Samples were analyzed by LC-MS/MS (without internal standard). Percentage remaining at each time point is calculated relative to the average peak area of the t=0 sample. Half-life (t½ in hours) is calculated from those data.

SGF stability and FASSIF stability. The stability of the prodrugs in simulated gastric fluid (SGF) in presence of pepsin and in fasted simulated intestinal fluid (FASSIF) supplemented with pancreatine and esterase was measured. Test compounds were incubated in vitro for up to 2 hours and samples were taken at different time points. Samples were analyzed for parent compound disappearance by LC-MS/MS. Percentage remaining at each time point is calculated relative to the average peak area of the t=0 sample. Half-life (t112 in hours) is calculated from those data.

Pharmacokinetics in rat. Prodrugs were administered orally to SD rats using aqueous solution at 5 mg/kg eq dose. Plasma samples were collected at different time points and the concentration of parent and prodrug was analyzed using LC-MS/MS. PK parameters were calculated using Phoenix WinNonlin 6.3. $C_{max}$ (ng/mL) and $AUC_{(0-last)}$ (ng·h/mL) were determined for both prodrug and parent.

TABLE 1

Permeability in MDCK-MDR1 cell line.

| Entry | Papp A->B + GF120918 | Papp A->B - GF120918 | Efflux ratio B->A/A -> B |
|---|---|---|---|
| 2 | 1.6 | 0.4 | 54 |
| 3 | 1.6 | <0.2 | >61 |
| 5 | 47 | 20 | 3.2 |
| 6 | 27.5 | 6.8 | 10 |
| 8 | 10 | <1 | >43 |
| 10 | 17 | 1.8 | 33 |

TABLE 2

Intrinsic clearance (CLint) in liver microsomes and hepatocytes.

| Entry | $CL_{int}$ rat liver microsomes | $CL_{int}$ human liver microsomes | $CL_{int}$ hepatocytes rat | $CL_{int}$ hepatocytes human |
|---|---|---|---|---|
| 2 | 18 | <7.7 | 20 | <1.9 |
| 3 | 178* | 297* | 110 | 17 |
| 5 | 141 | 14 | 280 | 80 |
| 6 | 25 | 18 | 120 | 33 |
| 8 | >347 | n.d. | >280 | >280 |
| 9 | 27 | 115 | n.d. | n.d. |
| 10 | >347* | 88-90 | n.d. | n.d. | n.d. = not done,
*an average of two data points

TABLE 3

Stability in simulated gastric fluid (SGF) and fasted simulated intestinal fluid (FASSIF) and stability in rat and human plasma.

| Entry | $t_{1/2}$ SGF (h) | $t_{1/2}$ FASSIF (h) | $t_{1/2}$ rat plasma (h) | $t_{1/2}$ human plasma (h) |
|---|---|---|---|---|
| 2 | >6 | >6 | >30 | >30 |
| 3 | >6 | >6 | >30 | >30 |
| 5 | >6 | >6 | >30 | >30 |
| 6 | >6 | >6 | >30 | >30 |
| 8 | 3.9 | 0.1 | <0.4 | 1 |
| 9 | 1 | 1.1 | <0.4 | <0.4 |
| 10 | 0.3 | 0.8 | 1.4 | 1.4 |

TABLE 4

Oral administration of 1 and prodrugs in rat.

| Entry | $C_{max}$ prodrug | $AUC_{(0-last)}$ prodrug | $C_{max}$ Compound 1 | $AUC_{(0-last)}$ Compound 1 |
|---|---|---|---|---|
| 1 | n.a. | n.a. | 177 | 486 |
| 2 | 1360 | 2567 | BQL | BQL |
| 5 | 88 | 144 | 37 | 60 |
| 6 | 129 | 206 | 47 | 114 | n.a. = not applicable

The invention claimed is:

1. A compound of formula (I)

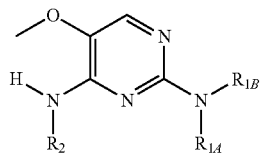

(I)

or a pharmaceutically acceptable salt, solvate or polymorph thereof, wherein
$R_{1A}$ is hydrogen or a substituted or unsubstituted $C_{1-3}$ alkyl,
$R_{1B}$ is selected from, a substituted or unsubstituted $C_{1-3}$ alkyl, heterocycle, or a substituted or unsubstituted phosphoramidate, and
$R_2$ is a $C_{1-8}$ alkyl optionally substituted by a hydroxyl group.

2. A compound according to claim 1 wherein $R_{1A}$ or $R_{1B}$ are a substituted or unsubstituted phosphoramidate and wherein $R_2$ is a $C_{1-6}$ alkyl substituted by a hydroxyl group.

3. A compound according to claim 1 wherein $R_{1A}$ or $R_{1B}$ are methyl and wherein $R_2$ is a $C_6$-alkyl substituted by a hydroxyl group.

4. A pharmaceutical composition comprising a compound of formula (I) or a pharmaceutically acceptable salt, solvate or polymorph thereof according to claim 1 together with one or more pharmaceutically acceptable excipients, diluents or carriers.

5. A compound according to claim 1 wherein $R_{1A}$ and $R_{1B}$ are a substituted or unsubstituted phosphoramidate and wherein $R_2$ is a $C_{1-6}$ alkyl substituted by a hydroxyl group.

6. A compound according to claim 1 wherein $R_{1A}$ and $R_{1B}$ are methyl and wherein $R_2$ is a $C_6$-alkyl substituted by a hydroxyl group.

7. A pharmaceutical composition comprising a compound according to claim 2 together with one or more pharmaceutically acceptable excipients, diluents or carriers.

8. A pharmaceutical composition comprising a compound according to claim 5 together with one or more pharmaceutically acceptable excipients, diluents or carriers.

9. A method for treating a virus infection, comprising administering to a subject in need thereof the pharmaceutical composition according to claim 4 in an effective amount to treat the virus infection.

10. A method for treating according to claim 9, wherein the virus infection is a hepatitis B infection.

11. A method for treating an immune disorder, comprising administering to a subject in need thereof the pharmaceutical composition according to claim 4 in an effective amount to treat the immune disorder.

12. A method for treating cancer, comprising administering to a subject in need thereof the pharmaceutical composition according to claim 4 in an effective amount to treat the cancer.

13. The compound of claim 1 selected from the group consisting of:

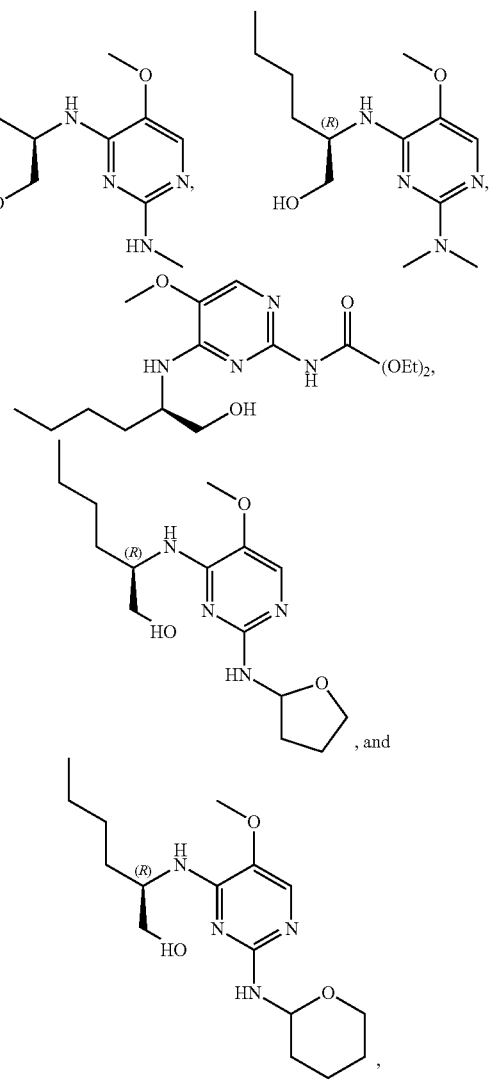

or a pharmaceutically acceptable salt thereof.

* * * * *